United States Patent [19]
Yudelson et al.

[11] Patent Number: 5,233,995
[45] Date of Patent: Aug. 10, 1993

[54] ENCAPSULATED PARTICLES USEFUL AS CONTRAST AGENTS IN ULTRASOUND AND X-RAY IMAGING COMPOSITIONS AND METHODS

[75] Inventors: Joseph S. Yudelson; Robert O. James, both of Rochester, N.Y.; Denis M. Bailey, Phoenixville, Pa.

[73] Assignee: Sterling Winthrop Inc., New York, N.Y.

[21] Appl. No.: 795,590

[22] Filed: Nov. 21, 1991

[51] Int. Cl.$^5$ .................. A61B 8/00; C07C 101/68
[52] U.S. Cl. .................. 128/662.02; 560/47; 424/5
[58] Field of Search ............ 128/662.02; 424/5, 9; 560/47

[56] References Cited

U.S. PATENT DOCUMENTS

| | | | |
|---|---|---|---|
| 3,119,858 | 1/1964 | Larsen | 560/47 |
| 3,128,301 | 4/1964 | Larsen et al. | 560/47 |
| 4,124,705 | 11/1978 | Rothman et al. | 514/58 |
| 4,376,802 | 11/1969 | Holtermann et al. | 562/457 |
| 4,567,034 | 1/1986 | Charles et al. | 424/5 |
| 4,572,203 | 2/1986 | Feinstein | 128/662.02 |
| 4,718,433 | 1/1988 | Feinstein | 128/662.02 |
| 4,774,958 | 10/1988 | Feinstein | 128/662.02 |
| 4,844,882 | 6/1989 | Widder et al. | 424/9 |

OTHER PUBLICATIONS

Bommer et al, Circulation 1981, 64:200–203.
Feinstein et al, J. Am. Coll. Cardiol 1984, 4:595–600.
Mattrey et al, Radiology 1987, 163:339–343.

*Primary Examiner*—Francis Jaworski
*Attorney, Agent, or Firm*—William J. Davis

[57] ABSTRACT

Stable particles comprising a core consisting of a water-insoluble ester or amide of 3,5-diacetamido-2,4,6-triiodobenzoic acid encapsulated with methyl cellulose, such particles having an average particle size of less than about 10 μm, dispersions containing such particles, and methods for the preparation thereof are disclosed. The particles are particularly useful as contrast agents for use in x-ray and ultrasound diagnostic imaging compositions and methods.

13 Claims, No Drawings

ENCAPSULATED PARTICLES USEFUL AS CONTRAST AGENTS IN ULTRASOUND AND X-RAY IMAGING COMPOSITIONS AND METHODS

FIELD OF INVENTION

This invention relates to novel encapsulated particles which are useful as contrast agents in ultrasound and x-ray diagnostic imaging compositions and methods.

BACKGROUND OF THE INVENTION

Medical diagnostic imaging techniques such as ultrasound imaging and x-ray imaging are extremely valuable tools for the early detection and diagnosis of various disease states of the human body. The use of contrast agents for image enhancement in medical diagnostic imaging procedures is widespread. An excellent background on image enhancement or contrast agents in medical imaging is provided by D. P. Swanson et al, Pharmaceuticals in Medical Imaging, 1990, MacMillan Publishing Company, the disclosure of which is hereby incorporated by reference in its entirety.

In x-ray imaging, transmitted radiation is used to produce a radiograph based upon tissue attenuation characteristics. X-rays pass through various tissues and are attenuated by scattering, i.e., reflection or refraction, or energy absorption. However, blood vessels and body organs, e.g., the liver, exhibit so little absorption of x-ray radiation that radiographs of these body portions are difficult to obtain. To overcome this problem, radiologists introduce an x-ray absorbing medium, i.e., a contrast agent, into body organs and vessels.

Computerized tomography (CT) scanning is a high contrast imaging technique which utilizes x-rays to produce tomographic images of the body's internal structures. Contrast agents used for this purpose must be capable of attenuating x-rays. Contrast agents which are extremely useful are those which are designed to be taken up preferentially by a portion of the body which is desired to be imaged by means of x-ray technology. This lowers the background noise and permits better contrast of the image of the body portion. There is a need for improved x-ray contrast agents for imaging specific portions of the body.

For example, currently there is no completely satisfactory x-ray contrast agent available for imaging the liver. Emulsions of iodinated oils such as iodinated ethyl esters of poppy seed oil and liposomes containing water soluble iodinated contrast agents have been proposed for liver visualization. However, emulsions tend to be unacceptably toxic and liposomes tend to require unacceptably large amounts of lipid to achieve adequate contrast enhancement.

In ultrasound imaging, short pulses of sound waves generated by an ultrasound transducer are directed at an anatomical region of interest. The ultrasound waves, like x-rays, pass through various tissues and are attenuated by scattering or energy absorption. However, in ultrasound imaging, the production of images is based on detecting the reflected portion of the attenuated sound waves.

Whether or not an ultrasound wave will be reflected at a given tissue or tissue component interface depends primarily on the acoustic impedance properties of the respective tissues or tissue components and the angle of incidence of the ultrasound wave with respect to the reflecting surface. Thus, at a given angle of incidence, the greater the difference between acoustic impedance values, the greater the ultrasound reflection. Consequently, the development of ultrasound contrast agents has been based upon attempts to maximize acoustic impedance differences at tissue or tissue component interfaces. Heretofore, the investigation of ultrasound contrast agents has been limited. However, some clinical success has been achieved using gas containing bubbles and lipid emulsions.

Gas containing bubbles and microbubbles, such as those described in U.S. Pat. No. 4,572,203; U.S. Pat. No. 4,718,433; U.S. Pat. No. 4,774,958 and U.S. Pat. No. 4,844,882; tend to be good reflectors of ultrasound waves due to the substantial difference in acoustic impedance between such bubbles and blood. Hand-injection approaches to the generation of intravascular bubbles to enhance ultrasound images generally result in an unsatisfactory, low intensity signal. Further, microbubbles produced by hand injection can provide ultrasound contrast enhancement of the right chamber of the heart, but are generally unable to survive passage through the capillary bed of the lung. Studies have reported that microbubbles of small diameter, i.e., less than 10 microns, produced by the sonification of various surfactant solutions or by precision gas injection microbubble techniques are capable of capillary transmission (Bommer et al, Circulation 1981, 64:200–203; Feinstein et al, J. Am. Coll. Cardiol. 1984, 3:595–600). However, the use of such agents for ultrasound enhancement of the left chamber of the heart following intravenous administration has been extremely limited, due to the lack of availability of precision microbubbles and surfactant formulations indicated and approved for ultrasound image enhancement. Furthermore, gas-containing bubble systems tend to be unstable when subjected to systolic blood pressures and shear. Thus, the overall safety of gas-containing bubble ultrasound contrast enhancement compositions remains a significant concern, particularly when such formulations are introduced into coronary arteries.

In addition to gas-containing bubble systems, lipid emulsions have been investigated as potential ultrasound contrast enhancement agents. Mattrey et al, Radiology, 1987, 163:339–343 have reported preliminary clinical success with the intravenous injection of a perfluorocarbon, i.e., perfluorodecalin-perfluorotripropylamine, emulsion. However, other dense lipid emulsions have failed to produce an increase in echogenicity. Furthermore, nonemulsified perfluorocarbons vaporize at body temperature. Thus, the ultrasound enhancement effects of perfluorocarbon emulsions may be related to breakdown of the emulsion in the RES cells and the subsequent release of perfluorocarbon vapor in the form of microbubbles. Consequently, this approach may not avoid the problems associated with gas containing bubbles.

Thus, there is a need for ultrasound contrast agents which are useful in diagnostic imaging of coronary vessels and the left chamber of the heart and which do not exhibit the problems of the prior art materials.

SUMMARY OF THE INVENTION

We have found that water-insoluble esters and amides of 3,5-diacetamido-2,4,6-triiodobenzoic acid can be dispersed as extremely fine particles by the use of methyl cellulose. Surprisingly, the particles become encapsulated by the methyl cellulose by an irreversible process which is not completely understood at the present time. Such particles are particularly useful as contrast agents for use in ultrasound and x-ray diagnostic imaging compositions and methods.

More particularly, in accordance with this invention, stable particles are provided comprising a core, consisting of a water-insoluble ester or amide of 3,5-diacetamido-2,4,6-triiodobenzoic acid, encapsulated with methyl cellulose, such particles having an average particle size of less than about 10 μm.

In another embodiment of this invention, there is provided a stable dispersion comprising the above-described particles.

In a further embodiment of this invention, there is provided a method for preparing the above-described particles comprising the steps of forming a first solution of an ester or an amide of 3,5-diacetamido-2,4,6-triiodobenzoic acid in a water-miscible solvent; forming a second solution comprising methyl cellulose and water; mixing the first and second solutions; sonicating the mixture so as to produce a stable dispersion; and isolating the particles.

In yet another embodiment of the invention, there is provided an ultrasound contrast composition comprising the above-described particles. Such composition is useful in a method for ultrasound diagnostic imaging when an effective contrast producing amount is administered to the body of a test subject.

In still another embodiment of the invention, there is provided an x-ray contrast composition comprising the above-described particles. Such composition is useful in a method for x-ray diagnostic imaging when an effective contrast producing amount is administered to the body of test subject.

It is an advantageous feature of this invention that novel encapsulated particles are provided which are useful echogenic agents for ultrasound examinations, particularly of the coronary vessels and left chamber of the heart. The particles reflect ultrasonic radiation and yet are small enough to pass through the capillary system. It is another advantageous feature of this invention that the aforementioned particles hydrolyze to a known acid form which is rapidly excreted from the vascular system. These particles do not exhibit the problems of prior art ultrasound contrast compositions containing gases or microbubbles.

Other advantages will become readily apparent upon reference to the following description of the preferred embodiments.

DESCRIPTION OF PREFERRED EMBODIMENTS

The invention is hereinafter described particularly in regard to preferred embodiments featuring particles comprising cores consisting of water-insoluble esters or amides of 3,5-diacetamido-2,4,6-triiodobenzoic acid encapsulated with methyl cellulose for use in x-ray and ultrasound diagnostic imaging compositions and techniques. In addition, the invention is believed to be useful in conjunction with other water-insoluble polyiodinated aromatic acids such as derivatives of 3-acetamido or 3,5-diacetamido substituted polyiodobenzoic acids.

The particles of this invention comprise a core preferably consisting of a water-insoluble ester or amide of 3,5-diacetamido-2,4,6-triiodobenzoic acid. In addition, it is believed that the core can consist of water insoluble polyiodinated aromatic compounds such as iodipamide and esters or amides of polyiodinated aromatic acids such as metrizoic acid, iothalamic acid, and trimesic acid. The water-insoluble species preferably comprises an ester or amide having the structural formula:

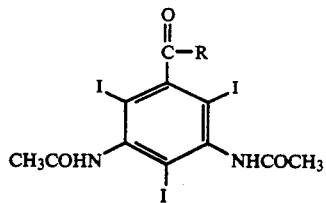

In formula 1 above, R is OR¹ or

wherein $R^1$ is alkyl; and
$R^2$ and $R^3$ are independently H or alkyl.

Each alkyl group can independently contain from 1-20, preferably 1-8, and more preferably, 1-4 carbon atoms. A particularly preferred compound has the formula 1 above wherein $R=OCH_2CH_3$, such compound being referred to herein as EEDA (the ethyl ester of diatrizoic acid).

The esters and amides useful in the practice of this invention are known compounds and/or can be prepared by techniques known in the art. For example, water insoluble esters and amides of iodinated aromatic acids can be prepared by conventional alkylation or amidation techniques. The above-noted acids and other acids which can be used as starting materials are commercially available and/or can be prepared by techniques known in the art.

The particles of this invention have a diameter of less than 10 μm, preferably less than 5 μm, and more preferably of less than 2 μm. Such preferred particles are of a size and composition such that they act as a reflector of ultrasonic radiation, yet readily pass through the capillary system.

It is particularly advantageous feature that the preferred particles of this invention hydrolyze to an acid form which is physiologically acceptable and rapidly excreted from the vascular system. The sodium salt of diatrizoic acid, i.e., formula 1 above wherein R=ONa, is a well known radiopaque material widely used commercially as a diagnostic aid in medical radiology. It is marketed by Sterling Drug Inc. under the trademark Hypaque ® Sodium. The x-ray imaging efficacy of the particles of the invention is not dependent on hydrolysis to the acid form.

The particles of the invention can be prepared by the above-described method which includes forming a first solution of an ester or amide of 3,5-diacetamido-2,4,6-triiodobenzoic acid in a water-miscible organic solvent. Suitable water-miscible solvents include N,N-dimethylformamide (DMF), formamide, acetamide and dimethyl sulfoxide.

A second solution can be prepared comprising methyl cellulose and water. The methyl cellulose preferably has a viscosity (measured at 2% solids and 25° C.) of less than about 200 cp. Grades of methyl cellulose having a viscosity greater than about 1500 cp did not yield fluid dispersions and resulted in discontinuous gels.

The relative weights of the ester or amide and methyl cellulose present in the reaction mixture must be such that the methyl cellulose is driven onto the surface of the ester or amide. Excellent results have been achieved at relative weights of about 45:55 and 30:70 in the reaction mixture.

The first and second solutions can then be mixed, e.g., by injecting the solution of the water-insoluble ester or amide into the aqueous methyl cellulose solution, to bring the species into intimate contact.

The mixture is subjected to ultrasonic radiation for a time and at an intensity sufficient to provide a stable dispersion. For example, the mixture can be subjected to ultrasonic energy for a time of at least several seconds to several minutes or longer. During sonication, the core of the particle becomes encapsulated with the methyl cellulose. Conventional ultrasonic generators, e.g., probe type generators, can be used at power levels from about 25 to 250 watts for relatively small solution volumes, e.g., 10 ml up to several hundred ml, such that the energy dissipated as heat is sufficient to raise the temperature of the solution to reaction temperatures. It is preferred that the temperature of the mixture increase to at least about 60° C. and preferably to about 70° C. to bring about the encapsulating reaction during sonication.

For convenience, the process can be carried out at ambient (atmospheric) pressures although it is contemplated that higher or lower pressures can be employed.

The particles can be isolated from the dispersion medium, i.e., the mixture of solutions, and/or purified by conventional separation techniques including, e.g., centrifugation and fractionation techniques. Particularly preferred is a centrifugation technique such as described in Example 1, inasmuch as it effectively separates the encapsulated particles from unattached methyl cellulose and any solvents, e.g., dimethylformamide, present which may be toxic.

The relative amounts by weight of the ester or amide and methyl cellulose in the purified encapsulated particle can be from about 50:50 to about 90:10. Preferred particles after purification consist of about 5 parts by weight of the ester or amide for each part by weight of methyl cellulose. Preferred dispersions in accordance with this invention comprise an aqueous dispersion medium and up to about 50 percent by weight of the above-described particles.

The above-described particles are effective contrast agents in x-ray and ultrasound contrast compositions. Such compositions comprise the above-described finely divided encapsulated particles dispersed in an aqueous liquid which serves as the carrier for the contrast agent. Preferably, the dispersions can be injected into the bloodstream and used for x-ray or ultrasound visualization of certain blood vessels or body organs. It is also contemplated that the particles can be formulated into liquid compositions suitable for oral administration when used for gastro-intestinal imaging applications.

The encapsulated particles can be mixed with one or more conventional additives used to control and enhance the properties of x-ray or ultrasound contrast agents. For example, thickening agents such as dextran or human serum albumin, buffers, viscosity regulating agents, suspending agents, peptizing agents, anti-clotting agents and other drugs, mixing agents and the like can be added. A partial listing of certain specific additives includes gums, sugars such as dextran, human serum albumin, gelatin, sodium alginate, agar, dextrin, pectin and sodium carboxymethyl cellulose. Such additives, as well as surface active agents, preservatives and the like can be incorporated into the compositions of the invention.

The invention provides a method for diagnostic imaging for use in medical procedures which comprises administering to the body of a test subject an effective contrast producing amount of the above-described x-ray contrast composition. Thereafter, at least a portion of the body containing the administered contrast agent is exposed to x-rays to produce an x-ray image pattern corresponding to the presence of the contrast agent. The image pattern can then be visualized. For example, the image pattern can be observed directly on an x-ray sensitive phosphor screen-silver halide photographic film combination, or any other x-ray visualization technique, such as computerized axial tomography, can be applied in a conventional manner. The particles of the present invention are particularly useful in contrast enhanced x-ray computerized tomography imaging applications.

It is contemplated that the primary utility of the above-described x-ray contrast composition is for diagnostic imaging of the liver. However, it is also contemplated that the x-ray contrast composition will be useful in angiography, e.g., imaging of blood vessels, due to the ability of the contrast agents to remain in the blood pool circulation in effective contrast enhancing amounts for extended periods of time, i.e., longer than a few minutes.

This invention also provides a method of ultrasound imaging for use in medical procedures which comprises administering to the body of a test subject, an effective contrast producing amount of the above-described ultrasound contrast composition. For example, such composition can be injected into a mammal to alter the acoustic properties of a predetermined area. Then the area including the predetermined area is ultrasonically scanned by techniques known in the art so as to obtain an enhanced image of the predetermined area.

The primary utility of the above-described ultrasound contrast composition is for diagnostic imaging of coronary vessels and the left chamber of the heart. The particles have a dense core of a water-insoluble ester or amide encapsulated with methyl cellulose enabling them to reflect ultrasonic radiation and yet are small enough to pass through the capillary system. Moreover, the particles hydrolyze to an acid form which is rapidly excreted from the vascular system and is physiologically well understood. It is contemplated that the ultrasound contrast compositions of the invention will also be useful in diagnostic imaging of the liver.

For the above-described diagnostic techniques the test subject can include, in addition to humans, mammalian species such as dogs, cats, monkeys, sheep, pigs, horses, bovine animals and the like.

The dose of the contrast agents administered can be selected according to techniques known to those skilled in the art so that a sufficient contrast effect is obtained.

Methyl cellulose exhibits inverse solubility-temperature behavior, i.e., methyl cellulose solutions gel when heated to a certain temperature. However, this gelation is reversible and the gels rapidly liquify as the temperature is lowered. Sonicating a methyl cellulose solution produces a phase separation as shown by a turbidity increase, but as the temperature is lowered to room conditions, the solution becomes clear as the methyl cellulose goes back into solution. Thus, it was surprising and unexpected that the particles described herein were irreversibly encapsulated with methyl cellulose. This is particularly so inasmuch as albumin, a protein that undergoes irreversible coagulation upon heating, did not produce stable dispersed particles when used under the conditions described above, and materials other than methyl cellulose tested resulted in unstable dispersions as described in the Comparative Examples which follow. While the applicants do not wish to be bound by theoretical mechanisms, it is hypothesized that a possibility exists of a specific interaction between the iodide containing core and the methyl cellulose.

The following examples further illustrate the invention.

EXAMPLES

Examples 1-2

Methyl Cellulose Encapsulated EEDA

Ten ml of a 1% (w/v) solution of methyl cellulose (Sigma, M6385) was placed in a small vial (4 ml) and placed under the horn (1.25 cm diameter) of a Sonifier Cell Disruptor, Model W185 (Heat Systems Ultrasonics, Inc.). The horn was positioned so that it was at the midway point in the solution. The power was turned on at the 75 watt level and 1 ml of a 8% DMF solution (w/v) of EEDA was injected directly under the horn. The mixture was sonicated for two minutes after which time the temperature had risen to 70°-72° C. A turbid dispersion resulted which showed no sign of sedimentation after several days standing.

The suspension was examined by disc centrifugation using a Shimadzu SA-CP3 centrifugal analyzer. Using the density of EEDA as 2.20 g/ml (without the encapsulating methyl cellulose), the median diameter was 0.16 $\mu$m. The data showed a distribution of 0.1 to 0.4 $\mu$m. If the density of the encapsulated particle was used, the resulting size distribution would be shifted to somewhat larger sizes (since the density of the EEDA plus methyl cellulose is lower than EEDA alone).

The suspension was analyzed by transient electric birefringence methods. A size distribution ranging from 0.2 to 1 $\mu$m was found with the peak of the distribution centering on 0.4 $\mu$m.

The suspension was examined by transmission electron microscopy. The micrographs showed that EEDA cores are encapsulated by a less electron dense shell. Diffraction examination of the core showed the cores to have presence of iodine. The cores were in the 0.5 $\mu$m diameter range and the shells appeared to be 1-2 $\mu$m.

The product obtained was dialyzed against deionized water for one week. The suspension which had become diluted to half of its original concentration and which was now free of DMF was still stable.

Example 1 was repeated using twice the amount of methyl cellulose (Example 2). Similar results were obtained.

Analysis of EEDA/Methyl Cellulose Particles

A suspension prepared as described in Example 1 was centrifuged at 12,000 g for 30 min. The gelatinous precipitate was rinsed with distilled water and recentrifuged two more times. The residue was dried at 80° C. overnight and analyzed. The results showed the particles to consist of (by wt) 5 parts of EEDA to each part of methyl cellulose.

Ultrasonic Scattering of EEDA/Methyl Cellulose Particles

A sample prepared as described in Example 2 was examined for echogenicity using a 7.5 Mhz radiation probe and an imager manufactured by Acoustic Imaging. A very good scattering pattern resulted which was 10-20 times that of a water control.

COMPARATIVE EXAMPLES A-K

Example 1 was repeated with lesser amounts of methyl cellulose, i.e., with one-half and one-quarter the amount. These examples (Comparative Examples A and B, respectively) resulted in unstable dispersions. Experiments similar to Example 1 were carried out except that the following materials were used in place of methyl cellulose.

| Comparative Examples | |
|---|---|
| C | Sorbitol |
| D | Carboxymethyl cellulose |
| E | Gelatin (calf) |
| F | Gelatin (pig) |
| G | Gelatin (bone) |
| H | Polyvinylpyrrolidone |
| I | Polyvinyl alcohol |
| J | Polyethylene glycol (various molecular weight grades) |
| K | Human serum albumin |

In none of these comparative examples was a stable dispersion obtained.

EXAMPLES 3-4 AND COMPARATIVE EXAMPLES L AND M EFFECT OF VISCOSITY OF METHYL CELLULOSE

Experiments similar to Example 1 were carried out with different viscosity grades of methyl cellulose.

| | Sigma Designation | Viscosity (cp) 2% 25° C. |
|---|---|---|
| Example 3 | M7140 | 15 |
| Example 4 | M6385 | 25 |
| Comparative Example L | M0387 | 1500 |
| Comparative Example M | M0512 | 4000 |

Good results were obtained with Examples 3 and 4. The higher viscosity grades did not give fluid dispersions and resulted in discontinuous gels (Comparative Examples L and M).

The invention has been described in detail with particular reference to certain preferred embodiments thereof, but it will be understood that variations and modifications can be effected within the spirit and scope of the invention.

What is claimed is:

1. Stable particles comprising 50 to 90 percent by weight of a core consisting of a water insoluble ester or amide of 3,5-diacetamido-2,4,6-triiodobenzoic acid irreversibly encapsulated with 10 to 50 percent by weight of methyl cellulose, said particles having an average particle size of less than 10 $\mu$m.

2. The particles of claim 1 wherein said water insoluble ester or amide has the structural formula:

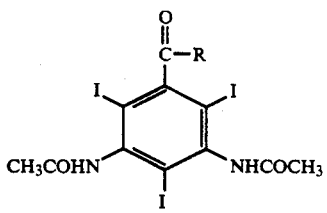

wherein R is OR¹ or

R¹ is alkyl; and

R² and R³ are independently H or alkyl.

3. The particles of claim 1 wherein said particles have an average particle size of less than about 2 μm.

4. The particles of claim 1 wherein said core has a diameter of less than 1 μm.

5. The particles of claim 1 wherein said core consists of the ethyl ester of 3,5-diacetamido-2,4,6-triiodobenzoic acid.

6. A stable dispersion comprising the particles of claim 1 and an aqueous dispersion medium.

7. An ultrasound contrast composition comprising the particles of claim 1 in an amount effective to enhance the contrast of an ultrasound image, and a carrier therefor.

8. A method for ultrasound diagnostic imaging which comprises administering to the body of a test subject an effective contrast producing amount of the ultrasound contrast composition defined in claim 7.

9. An x-ray contrast composition comprising the particles of claim 1 in an amount effective to enhance the contrast of an x-ray image, and a carrier therefor.

10. A method for x-ray diagnostic imaging which comprises administering to the body of a test subject an effective contrast producing amount of the x-ray contrast composition defined in claim 9.

11. A method of preparing particles comprising 50 to 90 percent by weight of a core consisting of a water insoluble ester or amide of 3,5-diacetamido-2,4,6-triiodobenzoic acid irreversibly encapsulated with 10 to 50 percent by weight of methyl cellulose, said particles having an average particle size of less than 10 μm, said method comprising the steps of:

forming a first solution of an ester or amide of 3,5-diacetamido-2,4,6-triiodobenzoic acid in a water-miscible solvent;

forming a second solution comprising methyl cellulose and water;

mixing said first and second solutions;

sonicating said mixture so as to produce a stable dispersion; and isolating said particles.

12. The method of claim 11 wherein the temperature of said mixture is at least 60° C.

13. The method of claim 11 wherein the viscosity of said methyl cellulose solution is less than about 200 cp.

* * * * *